United States Patent [19]
Wright

[11] Patent Number: 4,650,872
[45] Date of Patent: Mar. 17, 1987

[54] 5-CHLORO-S-TRIAZOLO[4,3-A]-PYRIDINE-7-CARBOXYLIC ACIDS, USEFUL AS ANTIALLERGIC AGENTS

[75] Inventor: Terry L. Wright, Antioch, Calif.

[73] Assignee: Merrell Dow Pharmaceuticals Inc., Cincinnati, Ohio

[21] Appl. No.: 761,464

[22] Filed: Aug. 1, 1985

[51] Int. Cl.$^4$ .......................................... C07D 471/04
[52] U.S. Cl. .................................................. 546/119
[58] Field of Search ........................................ 546/119

[56] References Cited
U.S. PATENT DOCUMENTS
3,597,423  8/1971  Wiedemann et al. ............... 546/119

OTHER PUBLICATIONS
W. W. Paudler & R. Brumbaugh, Chem. Ind., 24, 991 (1966).
K. T. Potts & H. R. Burton, J. Org. Chem., 31, 251 (1966).

Primary Examiner—Henry R. Jiles
Assistant Examiner—J. Richter
Attorney, Agent, or Firm—John J. Kolano

[57] ABSTRACT

5-Chloro-3-(substituted)-s-triazolo[4,3-a]pyridine-7-carboxylic acids useful as antiallergic agents are described herein. The compounds are prepared from an appropriate acyl 6-chloro-2-hydrazinopyridine, substituted at the 4-position with a trichloromethyl group or a cyano group, by reaction with polyphosphoric acid.

9 Claims, No Drawings

5-CHLORO-S-TRIAZOLO[4,3-A]-PYRIDINE-7-CARBOXYLIC ACIDS, USEFUL AS ANTIALLERGIC AGENTS

The present invention is directed to 5-chloro-s-triazolo[4,3-a]pyridine-7-carboxylic acid and related compounds substituted at the 3-position. More particularly, it relates to compounds having the following general formula

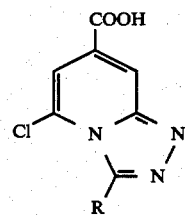

wherein R is hydrogen; alkyl of 1-7 carbon atoms optionally substituted by chlorine; phenyl, halophenyl or ($C_{1-4}$ alkyl)phenyl.

Examples of the alkyl groups are methyl, ethyl, propyl, n-butyl and n-heptyl. Examples of alkyl groups substituted by chlorine are chloromethyl, 2-chloroethyl and 3-chloropropyl. Halophenyl can be exemplified by fluorophenyl, chlorophenyl and bromophenyl. Examples of ($C_{1-4}$ alkyl)phenyl are methylphenyl and t-butylphenyl.

Equivalent for the purposes of this invention are the pharmaceutically acceptable salts and also the hydrates of the compounds and their salts. The term "pharmaceutically acceptable salt" as used herein is intended to include non-toxic cationic salts such as the alkali metal salts, e.g., sodium and potassium; alkaline earth metal salts such as calcium, magnesium or barium; salts with ammonia; and salts with organic bases, e.g., amines such as triethylamine, n-propylamine and tri-n-butylamine.

The compounds of the present invention are prepared from a hydrazide of the formula

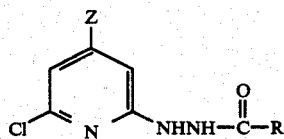

wherein R is defined as above and Z is —CN or —CCl$_3$. The hydrazide is heated with polyphosphoric acid at about 150°-160° C. to bring about cyclization to give the triazolo ring. At the same time, the —CN or the —CCl$_3$ groups are hydrolyzed to give a free carboxy group. Where desired, the free carboxylic acid can be converted to the corresponding salt by reaction with the appropriate base by standard procedures.

To obtain the hydrazide starting materials used above, a hydrazine of the formula

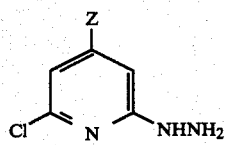

is reacted with an appropriate acid chloride. The process is carried out in the presence of a tertiary amine such as triethylamine or pyridine which neutralizes the acid formed in the reaction. An excess of this tertiary amine can serve as the solvent for the reaction or tetrahydrofuran or a similar inert substance can be used as the solvent.

When R is H, the hydrazide is obtained by heating the hydrazine with formic acid. This process actually gives a mixture of the desired hydrazide and the cyclization product of that hydrazide. No effort is made to separate the two compounds and, instead, the mixture is simply heated with polyphosphoric acid in the same way as the pure hydrazides.

The hydrazine starting material is obtained from 2,6-dichloro-4-(cyano or trichloromethyl)pyridine by reaction with hydrazine hydrate. One of the chlorines react with the hydrazine to give the substituted product.

The compounds of the present invention possess antiallergic activity. Thus, they are useful in the treatment of conditions in which antigen-antibody reactions are responsible for disease and particularly in the treatment of allergic diseases such as (but not limited to) extrinsic asthma, hay fever, urticaria, eczema or atopic dermatitis and upper respiratory conditions such as allergic rhinitis.

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and aqueous solutions for injection.

The nature of the pharmaceutical composition and the pharmaceutical carrier or diluent will, of course, depend on the desired route of administration, i.e., orally, parenterally or by inhalation. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maizestarch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of the present invention with conventional pharmaceutical vehicles may be employed, e.g., as an aerosol spray for inhalation, as an aqueous solution for intravenous injection or as an oily suspension for intramuscular injection. The compounds may also be administered by means of inhalers or other devices which permit the active compounds in the form of dry powders to come into direct contact with the lungs. Procedures for the preparation of compositions as discussed above are described in standard texts, such as *Remington's Pharmaceutical Sciences*, Mack Publishing Company, Easton, Pa.

The compounds of the present invention or pharmaceutical compositions thereof may be administered to human asthmatic patients by using single unit doses for inhalation which contain approximately 1-100 mg of active ingredient with multiple doses totaling up to about 400 mg/day of active ingredient. These values are illustrative only, however, and the physician of course will ultimately determine the dosage most suitable for a particular patient on the basis of factors such as age, weight, diagnosis, severity of the symptoms and the particular agent to be administered.

The present compounds were tested for antiallergic activity in the IgE mediated rat Passive Cutaneous Anaphylaxis (PCA) test. Disodium cromoglycate is active in this test when administered i.p. but not orally. The method can be described briefly as follows:

PCA Test Method

1. Antisera—Various standard methods described in the literature were used for the preparation of reaginic antisera to ovalbumin in either Hooded Lister or Brown Norway adult rats.

2. Animals—Adult male Sprague-Dawley or female Wistar Kyoto rats were used as antisera recipients in the test. The animals were allowed to acclimate for 5-14 days with food and water ad lib.

3. Sensitization—Recipient rats were passively sensitized by the intradermal injection of 100 microliters of two dilutions of antiserum (one injection on each side of the back). Sensitization occurred 48-72 hours prior to antigen challenge.

4. Administration of Test Compound—Four to six animals were used for each test compound/dilution. Compounds were homogenized in an appropriate carrier solution, and administered i.p. at 60 mg/kg 5 minutes prior to challenge or p.o. at 100 mg/kg 5 to 60 minutes prior to challenge.

5. Antigen Challenge and Reaction Evaluation—Ovalbumin (0.1-1.0 mg in a 0.5% solution of Evan's Blue Dye) in saline were given to each rat by i.v. administration. Thirty minutes later, the resultant PCA reactions were measured for average diameter and color intensity from the reflected surface of the skin. Test compound activity is expressed as percent inhibition based on control reactions.

When tested by the above procedure, the compounds of the present invention were active both i.p. and orally.

The following examples are presented to illustrate the present invention but they should not be construed as limiting in any way.

EXAMPLE 1

A solution of 30.6 g of 2,6-dichloropyridine-4-carbonitrile and 100 ml of dimethylsulfoxide was cooled to 0° C. in an ice bath and 26 g of hydrazine hydrate was added dropwise at a rate such that the temperature remained below 30° C. A heavy yellow precipitate formed and, after 2 hours, the reaction mixture was poured into 200 ml of water. The yellow solid was collected by filtration and dried to give 6-chloro-2-hydrazinopyridine-4-carbonitrile melting at about 208°-210° C.

EXAMPLE 2

A suspension of 5.0 g of 6-chloro-2-hydrazinopyridine-4-carbonitrile in 50 ml of pyridine was cooled to 0° C. in an ice bath and 3.1 g of acetyl chloride was added dropwise over a 10 minute period. The mixture became homogeneous after the addition and it was allowed to warm to ambient temperature. After 2 hours, the reaction mixture was poured into 180 ml of water and the precipitate which formed was separated by filtration and dried to give N-acetyl-N'-(6-chloro-4-cyano-2-pyridyl)hydrazine which was purified by recrystallization from ethanol.

When the above procedure was repeated using the appropriate acid chloride and hydrazine, the following compounds were obtained:

N-Benzoyl-N'-(6-chloro-4-cyano-2-pyridyl)hydrazine melting at about 238°-240° C. (dec.) after recrystallization from acetone.

N-Acetyl-N'-(6-chloro-4-trichloromethyl-2-pyridyl)hydrazine melting at about 198°-201° C. (dec.) after recrystallization from methanol.

N-(2-Bromobenzoyl)-N'-(6-chloro-4-trichloromethyl-2-pyridyl)hydrazine melting at about 226°-228° C. (dec.) after purification by washing several times with hot methanol.

EXAMPLE 3

A solution of 9.7 g of 3-chloropropionyl chloride in 20 ml of tetrahydrofuran was added dropwise to a stirred solution of 20 g of 6-chloro-2-hydrazino-4-trichloromethylpyridine and 11 ml of triethylamine at 0° C. A heavy precipitate of triethylamine hydrochloride formed almost immediately. After 2 hours, the reaction mixture was concentrated in vacuo to a volume of approximately 50 ml and poured into 500 ml of water with vigorous stirring. The tan precipitate which formed was separated by filtration and dried to give N-(3-chloropropionyl)-N'-(6-chloro-4-trichloromethyl-2-pyridyl)hydrazine melting at about 196°-199° C. (dec.) after recrystallization from methanol.

When the above procedure was repeated using the appropriate acid chloride, the following compounds were obtained:

N-Butanoyl-N'-(6-chloro-4-trichloromethyl-2-pyridyl)hydrazine melting at about 211°-212° C. after recrystallization from methanol.

N-Octanoyl-N'-(6-chloro-4-trichloromethyl-2-pyridyl)hydrazine melting at about 136°-138° C.

N-Chloroacetyl-N'-(6-chloro-4-trichloromethyl-2-pyridyl)hydrazine melting at about 177°-179° C. after recrystallization from acetone.

N-(4-Chlorobutanoyl)-N'-(6-chloro-4-trichloromethyl-2-pyridyl)hydrazine melting at about 183°-185° C.

N-Benzoyl-N'-(6-chloro-4-trichloromethyl-2-pyridyl)hydrazine melting at about 204°-206° C. (dec.).

N-(2-Fluorobenzoyl)-N'-(6-chloro-4-trichloromethyl-2-pyridyl)hydrazine melting at about 184°-188° C. (dec.) after recrystallization from acetone.

N-(4-Fluorobenzoyl)-N'-(6-chloro-4-trichloromethyl-2-pyridyl)hydrazine melting at about 223°-224° C. (dec.) after recrystallization from methanol.

N-[4-(t-Butyl)benzoyl]-N'-(6-chloro-4-trichloromethyl-2-pyridyl)hydrazine melting at about 216°-217° C. after recrystallization from diethyl ether.

EXAMPLE 4

A mixture of 10.5 g of 6-chloro-2-hydrazinopyridine-4-carbonitrile and 30 ml of 97% formic acid was heated at 90° C. for 5 hours. The reaction was quenched with 150 ml of water and the precipitate was separated by filtration to give a yellow product. The NMR spectrum of this solid showed that it was a mixture of the formylhydrazine and the corresponding cyclized product. This product mixture was added to 150 ml of polyphosphoric acid and heated to 160° C. After 3 hours, the dark brown solution was poured into 300 ml of water, aqueous sodium hydroxide was added to bring it to a pH of 5, and the mixture was allowed to stand for 16 hours. The yellow solid which formed was separated by filtration and dried and the resulting crude product was dissolved in aqueous sodium hydroxide and filtered. Acidification of the filtrate with concentrated hydrochloric acid produced a solid precipitate which was separated by filtration to give 5-chloro-s-triazolo[4,3-a]pyridine-7-carboxylic acid (1/6 hydrate) melting at about 249°–251° C. with decomposition.

EXAMPLE 5

N-Acetyl-N'-(6-chloro-4-cyano-2-pyridyl)hydrazine (5.6 g) was added to about 80 ml of polyphosphoric acid and the stirred mixture was heated to 150° C. The mixture become homogeneous at this temperature. After 3 hours, the dark brown solution was poured into 150 ml of water with rapid stirring. The aqueous solution was then cooled in ice and the resulting tan precipitate was separated by filtration, washed with water and dried to give 5-chloro-3-methyl-s-triazolo [4,3-a]pyridine-7-carboxylic acid.

EXAMPLE 6

A mixture of 1.4 g of N-acetyl-N'-(6-chloro-4-trichloromethyl-2-pyridyl)hydrazine and 30 ml of polyphosphoric acid was heated to 160° C. with stirring. At the reaction temperature, a vigorous foaming of the reaction mixture took place, presumably as a result of the evolution of hydrogen chloride gas formed from hydrolysis of the trichloromethyl group. The foaming subsided after about 10 minutes, and a clear brown solution resulted. After 3 hours at 160° C., the reaction mixture was poured into 200 ml of water and allowed to stand for 16 hours. No solid was present so aqueous sodium hydroxide was added to bring the pH to 5, whereupon a brown solid separated from the solution. This solid was separated by filtration, dissolved in aqueous sodium bicarbonate, treated with powdered charcoal, and filtered to give a pale-yellow solution. Acidification of the solution with aqueous hydrochloric acid caused a solid product to precipitate. This was separated by filtration and dried to give 5-chloro-3-methyl-s-triazolo[4,3-a]pyridine-7-carboxylic acid (hydrate) melting at about 259°–260° C. with decomposition. This compound has the following structural formula:

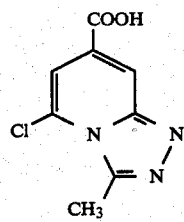

EXAMPLE 7

When the procedure of Example 6 was repeated using the appropriate hydrazine, the following compounds were obtained:

5-Chloro-3-phenyl-s-triazolo[4,3-a]pyridine-7-carboxylic acid (1/6 hydrate) melting at about 239°–243° C. with decomposition.

5-Chloro-3-propyl-s-triazolo[4,3-a]pyridine-7-carboxylic acid melting at about 200°–202° C. (dec.) after recrystallization from methanol.

5-Chloro-3-heptyl-s-triazolo[4,3-a]pyridine-7-carboxylic acid hydrate melting at about 149°–151° C. after recrystallization from methanol.

5-Chloro-3-chloromethyl-s-triazolo[4,3-a]pyridine-7-carboxylic acid melting at about 207°–213° C. (dec.) after recrystallization from methanol.

5-Chloro-3-(2-chloroethyl)-s-triazolo[4,3-a]pyridine-7-carboxylic acid hydrate melting at about 179°–185° C. This product was purified by dissolving it in aqueous base followed by reprecipitation with acid.

5-Chloro-3-(3-chloropropyl)-s-triazolo[4,3-a]pyridine-7-carboxylic acid.

5-Chloro-3-(2-bromophenyl)-s-triazolo[4,3-a]pyridine-7-carboxylic acid melting at about 235°–238° C. (dec.) after recrystallization from acetone.

5-Chloro-3-(2-fluorophenyl)-s-triazolo[4,3-a]pyridine-7-carboxylic acid melting at about 225°–255° C. (dec.) after recrystallization from methanol.

5-Chloro-3-(4-fluorophenyl)-s-triazolo[4,3-a]pyridine-7-carboxylic acid melting at about 252°–254° C. (dec.) after recrystallization from methanol.

5-Chloro-3-[4-(t-butyl)phenyl]-s-triazolo[4,3-a]pyridine-7-carboxylic acid melting at about 244°–245° C. with decomposition. In this case, the crude product was washed several times with water and dried and then washed with methylene chloride to give the purified product.

What is claimed is:

1. A compound of the formula

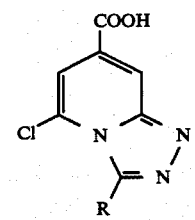

wherein R is hydrogen; alkyl of 1–7 carbon atoms optionally substituted by chlorine; phenyl, halophenyl or (C$_{1-4}$ alkyl)phenyl.

2. a compound according to claim 1 which has the formula

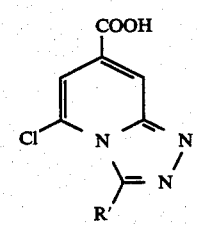

wherein R' is hydrogen or alkyl of 1–7 carbon atoms optionally substituted by chlorine.

3. A compound according to claim 1 which has the formula

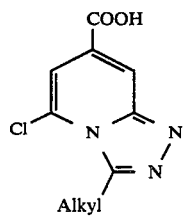

4. A compound according to claim 1 which is 5-chloro-s-triazolo[4,3-a]pyridine-7-carboxylic acid.

5. A compound according to claim 1 which is 5-chloro-3-methyl-s-triazolo[4,3-a]pyridine-7-carboxylic acid.

6. A compound according to claim 1 which is 5-chloro-3-(2-chloroethyl)-s-triazolo[4,3-a]pyridine-7-carboxylic acid.

7. A compound according to claim 1 which has the formula

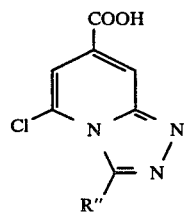

wherein R" is phenyl, halophenyl or ($C_{1-4}$ alkyl)phenyl.

8. A compound according to claim 1 which is 5-chloro-3-phenyl-s-triazolo[4,3-a]pyridine-7-carboxylic acid.

9. A compound according to claim 1 which is 5-chloro-3-(2-fluorophenyl)-s-triazolo[4,3-a]pyridine-7-carboxylic acid.

* * * * *